United States Patent [19]

Beuhler et al.

[11] Patent Number: 4,873,302

[45] Date of Patent: Oct. 10, 1989

[54] STYRENE-TERMINATED POLYETHERS OF POLYPHENOLS

[75] Inventors: Allyson Beuhler, Indian Head Park; James A. Wrezel, Buffalo Grove, both of Ill.

[73] Assignee: Allied-Signal Inc., Morris Township, Morris County, N.J.

[21] Appl. No.: 238,996

[22] Filed: Aug. 29, 1988

Related U.S. Application Data

[63] Continuation of Ser. No. 895,394, Aug. 11, 1986, abandoned.

[51] Int. Cl.$^4$ .............................................. C08F 16/12
[52] U.S. Cl. .................................................... 526/333
[58] Field of Search ......................................... 526/333

[56] References Cited

U.S. PATENT DOCUMENTS

| | | | |
|---|---|---|---|
| 3,951,888 | 4/1976 | Isayama et al. | 526/333 |
| 4,140,667 | 2/1979 | Preston et al. | 526/333 |
| 4,296,227 | 10/1981 | Seeburger et al. | 526/333 |
| 4,665,154 | 5/1987 | Varnell et al. | |

*Primary Examiner*—Joseph L. Schofer
*Assistant Examiner*—Peter D. Mulcahy
*Attorney, Agent, or Firm*—Raymond H. Nelson; Harold N. Wells; Jay P. Friedenson

[57] ABSTRACT

Styrene-terminated polyethers of polyphenols may be used as components in a laminate when coated on a reinforcement or substrate. The poly(vinyl benzyl ether) may be prepared by reacting a bisphenol with an alpha,omega-diahlosubstituted alkane and thereafter reacting the resultant product with vinyl benzyl chloride. The laminates which are prepared from these compounds may be employed in electric or electronic circuit boards and will possess desirable electrical and thermal properties as exemplified by a moderate-to-high glass transition temperature and a low dielectric constant.

7 Claims, No Drawings

STYRENE-TERMINATED POLYETHERS OF POLYPHENOLS

This is a continuation of application Ser. No. 895,394 filed Aug. 11, 1986, now abandoned.

BACKGROUND OF THE INVENTION

With the advent of sophisticated equipment in the electrical and electronic fields, it has become necessary that the components of the various pieces of equipment conform to high standards which are set forth in the specifications for these components. For example, circuit boards which are used in relatively complicated pieces of equipment such as main frame computers, must be of a relatively high standard of quality in order to function in an efficient manner for a longer period of time without deteriorating or breaking down, and thus causing an interruption in the function of the machine. This high quality of material is opposed to pieces of equipment requiring a lower standard of quality such as those used in personal computers, high quality television equipment, radios, etc.

Circuit boards upon which a circuit is etched or implanted usually comprise a laminate which is composed of a synthetic polymeric substance which possesses desirable characteristics such as thermal stability, low coefficient of thermal expansion, dimensional stability, low dielectric constant, solvent resistance, low moisture absorption, etc. and a suitable reinforcement matrix, such as glass, quartz, graphite, Kevlar, etc.

As will hereinafter be shown, it has now been discovered that a styrene-terminated polyether of a polyphenol may be synthesized and thermally cured to form a highly cross-linked network. The styrene-terminated material will comprise a processable material which possesses desirable characteristics of the type hereinbefore set forth, the aforementioned compound containing a distribution of oligomers of various molecular weights which provide proper balance among thermal properties (i.e. $T_g$, expansion coefficient), mechanical properties (i.e. ductility) and processability (i.e. viscosity, resin content, gel time).

BRIEF SUMMARY OF THE INVENTION

This invention relates to cross-linkable, styrene-terminated polyethers of a polyphenol. More specifically, the invention is concerned with these cross-linkable, styrene-terminated polyethers which may be used to coat and/or impregnate a substrate which is thereafter cured and utilized in circuit board laminates and dielectric coatings, the use thereof being attributable to the desirable characteristics which are possessed by these polymeric compositions of matter. The particular characteristics of the polymer dielectric and reinforcing components which go to make up the circuit boards contribute to the electrical/electronic performance of the printed circuit boards. For example, a lowering of the dielectric constant in the polymer matrix reduces the signal delay time, "crosstalk" and line capacitance. This will allow a high signal propogation velocity and, in addition, provide a potential to increase the circuit trace density and number of functions per board. The polymeric matrix of the present invention possesses a lower dielectric constant than that which is possessed by thermosetting polyimide or epoxy matrices which are used as the standards by the industry for electrical laminates.

Another desirable characteristic of a polymer matrix for use in circuit boards is that the coefficient of thermal expansion should be relatively low in order to reduce the mismatch of thermal expansions with the electronic components and the glass reinforced laminate. Furthermore, the thermal stability of the polymer matrix must be relatively high in nature inasmuch as the matrix must possess the ability to withstand soldering temperatures without melting or degrading.

In addition to the aforesaid desirable characteristics, the product of the present invention will be resistant to dissolution or decomposition, due to the action of a solvent on the circuit board which may form one of the end products in which the styrene-terminated polyether may be employed. For example, this is of particular importance when a solvent such as methylene chloride is employed in a subsequent degreasing process during the soldering stage which is one of the steps in preparing copper clad or multilayer boards.

It is therefore an object of this invention to provide styrene-terminated polyethers of polyphenols.

Another object of this invention is to prepare styrene-terminated polyethers of polyphenols which are cured to form highly cross-linked networks which are useful as a component in circuit board laminates.

In one aspect, an embodiment of this invention resides in a poly(vinyl benzyl ether) of a polyphenol which possesses the generic structure:

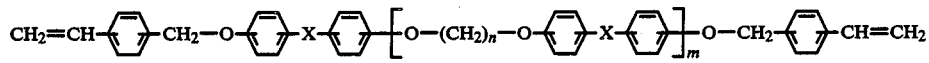

in which X is selected from the group consisting of S, $SO_2$, O and straight or branched chain alkyl radicals containing from 1 to about 6 carbon atoms, n is an integer of from 1 to about 8 and m is in a range of from 0 to about 10.

Another embodiment of this invention is found in a process for the production of a poly(vinyl benzyl ether) of a polyphenol which comprises reacting a bisphenol having the generic formula:

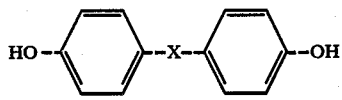

in which X is selected from the group consisting of S, $SO_2$, O and straight or branched chain alkyl radicals containing from 1 to about 6 carbon atoms with an alpha, omega-dihalosubstituted alkane containing from 1 to about 8 carbon atoms at reaction conditions, thereafter reacting the resultant reaction product with vinyl benzyl chloride, and recovering the resultant poly(vinyl benzyl ether) of a polyphenol.

A specific embodiment of this invention is found in a process for the production of a poly(vinyl benzyl ether) of a polyphenol which comprises reacting bisphenol A with 1,6-dibromohexane in the presence of a phase transfer catalyst comprising tetrabutylammonium hydrogen sulfate at a temperature in the range of from about 50° C. to about 150° C. and a pressure in the range of from about atmospheric to about 100 atmospheres, thereafter reacting the resultant reaction product with vinyl benzyl chloride and recovering the resultant poly(vinyl benzyl ether) of a polyphenol.

Other objects and embodiments will be found in the further detailed description of the invention.

DETAILED DESCRIPTION OF THE INVENTION

As hereinbefore set forth, the present invention is concerned with cross-linked polyethers of polyphenols which will possess desirable characteristics. In the electronic equipment area, it is necessary to utilize, as circuit boards in electronic circuitry, compositions of matter which possess desirable characteristics. The circuit boards are usually comprised of laminates in which a resin is impregnated on a reinforcement or substrate such as glass cloth, paper, Kevlar, quartz, graphite, etc. The various resins which are employed to provide the circuitry may be from many original sources. For example, thermosets are resins which require a curing step to form a cross-linked network structure. In general, the thermoset plastics possess a good resistance to the action of solvents. However, they also possess an undesirable characteristic in that their low resin tensile strength and fracture toughness limits the design strength capability of the resin to a certain degree. Another type of polymer which may be employed comprises a thermoplastic type of polymer which possesses a greater degree of toughness than does the thermoset resin. However, while this is a desirable characteristic, the thermoplastic also has inherent disadvantages in that (1) most thermoplastics must be heated to or above the melting point of the plastic in order to provide sufficient viscosity to allow a processing of said plastic, and (2) most thermoplastics are sensitive to solvents used in the circuit etching process. The material of the present invention combines the desirable characteristics of thermosets and thermoplastics in one material, as the density of cross-links being a function of the molecular weight of the poly(vinyl benzyl ether) is significantly lower than most commercially available thermoset materials. Thus, the lower cross-link density imparts more thermoplastic character to the composite.

In order to overcome the disadvantages which are possessed by the various types of polymers previously discussed, it is necessary to provide a polymer which will exhibit the desirable characteristics such as low dielectric constant, low dissipation factors, as well as a high resistance to solvents. In this respect the styrene-terminated polyethers of the present invention will fulfill the requirements in that the poly(vinyl benzyl ether) of the polyphenols which are formed according to the process hereinafter set forth, may be reacted through the vinyl groups to form a highly cross-linked thermoset polymer. In addition, the combination of the ether and the hydrocarbon structural units will impart a low dielectric constant to the crosslinked polymer. The molecular weight of the poly(vinyl benzyl ether) can be tailored to provide (1) the proper processability (i.e. melt viscosity, B-stage prepreg resin content, gel time) required for manufacture of printed circuit boards, and (2) impact toughness for structural integrity and proper ductility.

The styrene-terminated polyethers of polyphenols will comprise compounds having the generic structure:

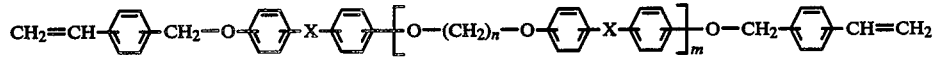

in which X is selected from the group consisting of S, SO$_2$, O and straight or branched chain alkyl radicals containing from 1 to about 6 carbon atoms, n is an integer of from 1 to about 8 and m is in a range of from 0 to about 10. These compounds may be prepared by reacting a bisphenol which has the generic formula:

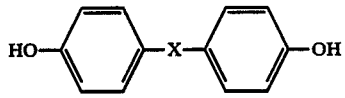

in which X is selected from the group consisting of S, SO$_2$, O and straight or branched chain alkyl radicals containing from 1 to about 6 carbon atoms with an alpha, omega-dihalo-substituted alkane containing from 1 to about 8 carbon atoms at reaction conditions, thereafter reacting the resultant reaction product with vinyl benzyl chloride, and recovering the resultant poly(vinyl benzyl ether) of a polyphenol. The resultant reaction product may be cured into an insoluble, thermoset product either thermally or in the presence of a free-radical initiator such as benzoyl peroxide at elevated temperature.

The reaction between the bisphenol and the alpha,omegadihalosubstituted alkane is effected at reaction conditions which will include a temperature in the range of from about 50° to about 150° C. and a pressure in the range of from about atmospheric to about 100 atmospheres. In the present embodiment of the invention, the reaction is effected in the presence of a phase transfer catalyst, some specific examples of these catalysts including tetrabutylammonium hydrogen sulfate, trimethylbenzylammonium chloride, tetra-n-butylammonium chloride, triethylbenzylammonium chloride hydrogen sulfate. In addition, the medium in which the reaction takes place is basic in nature, such basicity being provided for by the presence of an alkaline compound such as sodium hydroxide, potassium hydroxide, lithium hydroxide, ammonium hydroxide, etc.

The ratio of the reactants which are present to prepare the desired compound may vary over a relatively wide range and may be varied to provide a particular and desired molecular weight and/or molecular weight distribution of the final product. In this respect, it is a desirable feature that the product which is obtained by the reaction of the present process exhibit a broad molecular weight distribution and not be monodisperse in order that the proper reactivity, solution viscosity, and resin content/flow can be obtained for manufacture of printed circuit boards. In this respect, in the preferred embodiment of the invention, the particular bisphenol which is used as one component of the reaction mixture will be present in an excess over the dihalosubstituted alkane, said bisphenol being present in a mole ratio of from about 1.1:1 to about 50:1 moles of phenolic OH to moles of dihalosubstituted alkane, and preferably in a ratio in the range of from about 1.5:1 to about 10:1. Likewise, the vinyl benzyl chloride is also present in an excess over the phenolic OH compound, said vinyl benzyl chloride being present in a ratio in the range of from about 1.1:1 to about 50:1 moles of vinyl benzyl chloride per mole of phenolic OH, preferably in a range of from about 1.1:1 to about 10:1.

Some specific examples of bisphenol compounds which may be utilized as a starting material to prepare the desired compound of the present invention will include p,p'-dihydroxydiphenyl methane, p,p'-dihydroxydiphenyl ethane, p,p'-dihydroxydiphenyldimethyl methane (bisphenol A), p,p'-dihydroxydiphenyl ether, p,p'-dihydroxydiphenyl thioether, p,p'-dihydroxydiphenyl sulfoxide, o,o'-dihydroxydiphenyl methane, o,o'-dihydroxydiphenyl ethane, o,o'-dihydroxydiphenyldimethyl methane, o,o'-dihydroxydiphenyl ether, o,o'-dihYdroxydiphenyl thioether, o,o'-dihydroxydiphenyl sulfoxide, m,m'-dihydroxydiphenyl methane, m,m'-dihydroxydiphenyl ethane, m,m'-dihydroxydiphenyldimethyl methane, m,m'-dihydroxydiphenyl ether, m,m'-dihydroxydiphenyl thioether, m,m'-dihydroxydiphenyl sulfoxide.

Specific examples of alpha, omega-dihalosubstituted alkanes which contain from 1 to about 8 carbon atoms which may be reacted with the aforementioned bisphenols, will include dichloromethane, dibromomethane, 1,2-dichloroethane, 1,2-dibromoethane, 1,3-dichloropropane, 1,3-dibromopropane, 1,4-dichlorobutane, 1,4-dibromobutane, 1,5-dichloropentane, 1,5-dibromopentane, 1,6-dichlorohexane, 1,6-dibromohexane, 1,7-dichloroheptane, 1,7 dibromoheptane, 1,8-dichlorooctane, 1,8 dibromooctane.

It is to be understood that the aforementioned bisphenols and alpha, omega-dihalosubstituted alkanes are only representative of the type of compounds which may be employed and that the present invention is not necessarily limited thereto.

The styrene-terminated polyether of a polyphenol may be prepared in any suitable manner of operation which is known in the art. For example, in one method of preparation, a desired amount of a bisphenol and an alpha, omega-dihalosubstituted alkane may be placed in an appropriate mixing apparatus along with a solvent such as benzene, toluene, the xylenes, cyclohexane, etc. and an alkaline material to provide the basicity for the reaction medium. In addition, the reaction mixture will also include, if so desired, a phase transfer catalyst of the type hereinbefore set forth in greater detail. The mixture is thoroughly admixed for a predetermined time at reaction conditions which will include a temperature in the range of from about 50° C. to about 150° C. and at pressures in the range of from about atmospheric to about 100 atmospheres. It is to be understood that, in the event the reaction is to be effected at elevated pressures, a proper pressure resistant vessel such as an autoclave will be employed for the reaction. After allowing the reaction to proceed for the aforesaid predetermined period of time, the mixture is then allowed to cool to a temperature of less than 50° C. in order to prevent a premature polymerization of the third component of the product, namely the vinyl benzyl chloride. After reaching a temperature less than 50° C., the vinyl benzyl chloride is then added and the mixture stirred. After allowing the styrene-end capping reaction to proceed to completion, the reaction mixture is recovered and the desired product comprising the poly(vinyl benzyl ether) of a polyphenol is recovered by separation from any unreacted starting materials, said separation being effected by conventional means as exemplified by fractional distillation, filtration, reprecipitation into a nonsolvent (i.e. methanol), etc. As was hereinbefore set forth, by varying the ratio of the reactants, it is possible to control the molecular weight and molecular weight distribution of the product. The various molecular weight fractions which are present in the reaction product will contribute to the desirable characteristics of the final composition. For example, when referring to the generic structure of the homopolymer, when m has a relatively low value such as 0, 1 or 2, the cured material will possess a high cross-linked density, very high glass transition, low thermal expansion, excellent dimensional stability and an excellent resistance to solvents. Likewise, when m has a relatively high value such as 8, 9 or 10, the final composite will possess an improved resins solids content when in the B-stage, that is, more resin may be impregnated onto a substrate such as glass cloth; improved processability, that is, an improved viscosity in the B-stage for proper resin flow with loss of crystallinity; and an improved thermoplastic-like impact toughness or ductility, as well as a somewhat lower glass transition temperature.

It is also contemplated within the scope of this invention that the poly(vinyl benzyl ether) may be prepared in a continuous manner of operation. When this type of operation is employed, the bisphenol and the alpha,omega-dihalosubstituted alkane are continuously charged to a reaction zone along with the solvent, alkaline material and phase transfer catalyst, said reaction zone being maintained at the proper operating conditions of temperature and pressure. After passage through the reaction zone, the reactor effluent is continuously withdrawn, cooled to a predetermined temperature level and thereafter continuously charged to a second reaction zone wherein it is contacted with a continuous stream of vinyl benzyl chloride. Again, after passage through this zone which is also maintained at predetermined operating conditions of temperature and pressure, the reactor effluent is continuously withdrawn from the second reaction zone and the desired poly(vinyl benzyl ether) separated and recovered by conventional means.

The poly(vinyl benzyl ether) of a polyphenol which has been prepared according to any of the methods hereinbefore set forth may then be injection molded by an RIM process or compression molded at elevated temperature and utilized as a molded article of commerce. If so desired, a solution of the material may be coated on an appropriate reinforcement or substrate such as glass cloth, paper, graphite, polyaramid, etc. and treated at an elevated temperature of from about 150° C. to about 180° C. for a relatively short period of time, which may range from about 1 to about 10 minutes to obtain a prepreg. The resulting prepreg may then be stacked by pressing a predetermined number of sheets of the prepreg and pressing the stack in a heated press to form a desired laminate. The pressing of the prepreg may be effected for a period of time ranging from about 1 to about 24 hours in duration at an elevated temperature ranging from about 150° to about 200° C., at a pressure in the range of from about 500 to about 1,000 pounds per square inch gauge. Following the pressing, the laminate is then subjected to a postcure which is effected at a temperature in the range of from about 200° to about 260° C. for a period of time which may range from about 3 to about 6 hours in duration.

The following examples are given for purposes of illustrating the curing process and resultant properties for a poly(vinyl benzyl ether) of a polyphenol and to a process for the preparation of these compounds. However, it is to be understood that these examples are given merely for purposes of illustration and that the present invention is not necessarily limited thereto.

EXAMPLE I

In this example, a reaction medium comprising 176 grams of sodium hydroxide in 350 milliliters of water, 120 grams of tetrabutylammonium hydrogen sulfate and 400 milliliters of toluene was added to 50 grams (0.220 moles) of bisphenol A and 27 grams (0.110 moles) of 1,6-dibromohexane. The mixture was heated to a temperature of 80° C. with vigorous stirring of the reactants and allowed to react for a period of one hour. At the end of this time heating was discontinued and the reaction mixture was allowed to cool to a temperature of 40° C., said cooling being accomplished during a period of one hour. Following this, 34 grams (0.220 moles) of vinyl benzyl chloride (60/40 meta/para isomer mixture) were added, the solution turning a blueish color. The reaction was allowed to stand for a period of 48 hours with continuous stirring, at the end of which time the poly(vinyl benzyl ether) compound was recovered. Analysis of the resinous product disclosed that it had a DSC (Differential Scanning Calorimetry) glass transition temperature of 62° C. The number-average molecular weight of the compound as determined by GPC (Gel Permeation Chromatography) was 1593 g/mole; Weight-average molecular weight was 2531 g/mole and the dispersity index was 1.6. Other tests determined the heat of the polymerization was 102 joules/gram, as determined by DSC. This poly(vinyl benzyl ether) was cured thermally as a neat resin casting (from chloroform) using a cure cycle as follows—14 hours at 100° C. and 5 hours at 200° C. DSC revealed a glass transition at 79° C. for the fully cured material. TMA (Thermomechanical Analysis) indicated a softening point of 68° C., and thermal expansivity up to the softening point of 52 ppm°C$^{-1}$. The neat casting possessed a dielectric constant of 2.40 and a dissipation factor of 0.002 (1 MHz 23° C., 0% humidity).

EXAMPLE II

In a manner similar to that set forth in Example I above, p,p'-dihydroxydiphenyl ether and 1,6-dibromohexane in a mole ratio of 2:1 may be reacted in a basic toluene medium containing a phase transfer agent comprising trimethylbenzylammonium chloride at a temperature of 80° C. After allowing the reaction to proceed for a period of one hour at this temperature, the reaction mixture is cooled and, after reaching 40° C., vinyl benzyl chloride is added. The mixture is continuously stirred for a period of about 48 hours, following which the desired poly(vinyl benzyl ether) is recovered.

EXAMPLE III

In like manner, an excess of p,p'-dihydroxydiphenyl thioether and 1,8-dichlorooctane are reacted at a temperature of 80° C. for a period of 1 hour. At the end of this period, the mixture is cooled to a temperature of 40° C. and an excess of vinyl benzyl chloride based on the phenolic OH is added to said mixture. The reaction is allowed to proceed for a period of 48 hours with continuous stirring, following which the poly(vinyl benzyl ether) is recovered.

We claim as our invention:

1. A poly(vinyl benzyl ether) of a polyphenol which possesses the generic structure:

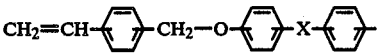

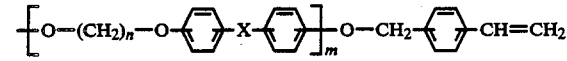

in which X is selected from the group consisting of S, SO$_2$, O and straight or branched chain alkyl radicals containing from 1 to about 6 carbon atoms, n is an integer of from 1 to about 8 and m is in a range of from 1 to about 10.

2. The poly(vinyl benzyl ether) of a polyphenol as set forth in claim 1 in which X is O.

3. The poly(vinyl benzyl ether) of a polyphenol as set forth in claim 1 in which X is methyl.

4. The poly(vinyl benzyl ether) of a polyphenol as set forth in claim 1 in which X is isopropyl.

5. The poly(vinyl benzyl ether) of a polyphenol as set forth in claim 1 in which n is 4.

6. The poly(vinyl benzyl ether) of a polyphenol as set forth in claim 1 in which n is 6.

7. The poly(vinyl benzyl ether) of a polyphenol as set forth in claim 1 in which n is 8.

* * * * *